United States Patent
Zambounis et al.

(10) Patent No.: US 6,359,122 B1
(45) Date of Patent: Mar. 19, 2002

(54) PYROCARBONIC ACID DIESTERS AND THE PREPARATION AND USE THEREOF

(75) Inventors: John Zambounis, Basle; Véronique Hall-Goulle, Bern, both of (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/767,313

(22) Filed: Jan. 23, 2001

Related U.S. Application Data

(62) Division of application No. 09/006,360, filed on Jan. 13, 1998, now Pat. No. 6,222,047, which is a division of application No. 08/681,205, filed on Jul. 22, 1996, now Pat. No. 5,750,758.

(30) Foreign Application Priority Data

Jul. 28, 1995 (CH) .............................................. 2222/95

(51) Int. Cl.⁷ ...................... C07D 273/04; C09B 29/34; C09B 19/02; C09B 7/02; C09B 48/00
(52) U.S. Cl. ........................... 534/860; 544/65; 546/53; 548/457
(58) Field of Search ......................... 534/860; 544/65; 546/53; 548/457

(56) References Cited

U.S. PATENT DOCUMENTS

| | | |
|---|---|---|
| 3,263,484 A | 8/1966 | Watson et al. |
| 3,732,722 A | 5/1973 | Norem et al. |
| 3,985,720 A * | 10/1976 | Manner et al. ............. 526/220 |
| 4,095,453 A | 6/1978 | Woo |
| 4,330,933 A | 5/1982 | Bullinger et al. |
| 4,350,466 A | 9/1982 | Bahr et al. |
| 4,783,174 A | 11/1988 | Gmelin et al. |
| 5,033,866 A | 7/1991 | Kehl et al. |
| 5,151,542 A * | 9/1992 | Kurimoto et al. ............ 558/277 |
| 5,224,775 A | 7/1993 | Reading et al. |
| 5,288,147 A | 2/1994 | Schaefer et al. |
| 5,599,104 A | 2/1997 | Nakamura et al. |
| 5,750,758 A * | 5/1998 | Zambounis et al. ......... 558/276 |
| 5,842,788 A | 12/1998 | Danley et al. |
| 6,222,047 B1 * | 4/2001 | Zambounis et al. ........ 548/453 |

FOREIGN PATENT DOCUMENTS

| | | |
|---|---|---|
| EP | 0468404 | 1/1992 |
| EP | o-468404 * | 1/1992 |

OTHER PUBLICATIONS

"A Differential Scanning Calorimeter for Quantitative Differential Thermal Analysis", E.S. Watson and M.J. O'Neill, Analytical Chemistry vol. 36, No. 7, pp. 1233–1238 (Jun. 1994).
"The Analysis of Temperature Controlled Scanning Calorimeter", M.J. O'Neill, Analytical Chemistry vol. 36, No. 7, pp. 1238–1245 (Jun. 1994).
"Differential Scanning Calorimetry an Introduction for Practicioners", G. Hohne, W. Hemminger, and H.J. Fammersheim (Springer–Verlag 1996) Chapters 2–3.

\* cited by examiner

*Primary Examiner*—Floyd D. Higel
*Assistant Examiner*—Golam M. M. Shameem
(74) *Attorney, Agent, or Firm*—David R. Crichton

(57) ABSTRACT

The invention relates to the preparation of pyrocarbonic acid diesters by an improved process and to the novel pyrocarbonic acid diesters prepared according to said process as well as to the use thereof.

The core of the invention is a process for the preparation of a pyrocarbonic acid diester of formula (I)

(I)

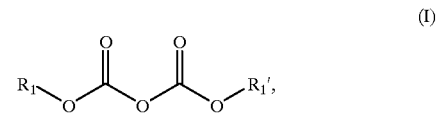

wherein $R_1$ and $R_1'$ are each independently of the other branched or straight-chain $C_1$–$C_{24}$alkyl, $C_3$–$C_{24}$alkenyl, $C_3$–$C_{24}$alkynyl, $C_4$–$C_{12}$cycloalkyl, $C_4$–$C_{12}$cycloalkenyl or $C_7$–$C_{24}$aralkyl, each of which is unsubstituted or substituted by one or more than one substituent which is inert under the reaction conditions, by reacting at least one ester carbonate of formula (II)

(II)

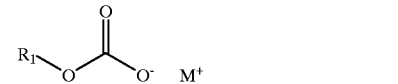

with 40–50 mol % of a sulfochloride of formula (IV)

(IV)

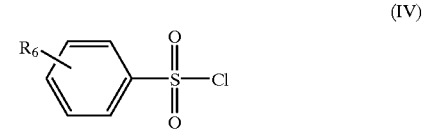

in the presence of 0.8–5 mol % of a catalyst of formula (V)

(V)

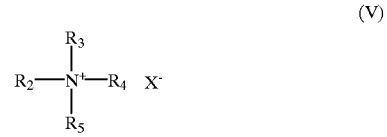

and with minor amounts of a heterocyclic aromatic amine in a nonpolar inert solvent, in which process the amount of heterocyclic aromatic amine is 1–3 mol % and the reaction is carried out in the temperature range from –10° C. to +25° C., all molar amounts being based on 100 mol % of ester carbonate of formula (II).

5 Claims, No Drawings

PYROCARBONIC ACID DIESTERS AND THE PREPARATION AND USE THEREOF

This application is a divisional of Ser. No. 09/006,360 filed on Jan. 13, 1998 now U.S. Pat. No. 6,222,047, which is a divisional of Ser. No. 08/681,205 filed on Jul. 22, 1996 now U.S. Pat. No. 5,750,758.

The present invention relates to the preparation of pyrocarbonic acid diesters by an improved process and to the novel pyrocarbonic acid diesters prepared according to said process as well as to the use thereof. The products are obtained in high yield and are of very high purity.

Pyrocarbonic acid diesters themselves are active compounds and are used, for example, as antiseptic agents for food. In addition, specific pyrocarbonic acid diesters, such as di-tert-butyl dicarbonate (DIBOC), are important fine chemicals, e.g. for introducing protective groups such as carbonate into alcohols, thiocarbonate into thiols or, in particular, urethane into amines or amides. Such groups are distinguished in that they are stable under normal conditions but can nevertheless be separated, for example hydrolytically or thermally, with reconversion of the original functions.

Substances which utilise said properties for technical purposes are known from EP 648 770 and EP 648 817. However, in contradistinction to standard tert-butyl urethanes prepared from DIBOC, more precise demands are made in such cases on the properties, in particular on the thermal properties. There is therefore a need for novel pyrocarbonic acid diesters as synthesis building blocks.

In view of the importance as food additives and fine chemicals, the most stringent demands are made on DIBOC and other dicarbonates with respect to purity. Many efforts have therefore been made to prepare DIBOC in ever enhanced quality and yield. This is complicated by DIBOC being thermally instable, as is indicated in J. Org. Chem. 43, 2410 (1978).

DIBOC can be prepared by two fundamentally different processes. In the first process, which is described in Org. Synth. 57, 45 (1975) and JP-88/051358, tert-butyl carbonate is reacted with phosgene to di-tert-butyl tricarbonate which is then decarboxylated in the presence of a tertiary amine (for example 1,4-diazabicyclo[2.2.2]octane) as catalyst, according to JP-91/356445 preferably with the addition of a phase transfer catalyst. In JP-92/310646, the tertiary amine is pyridine in a non-specific amount. According to JP-89/186847 it is also possible to use thionyl chloride instead of phosgene.

In the second, and generally preferred, process according to Zh. Org. Khim. 15/1, 106 (1975), tert-butyl carbonate is reacted with an acid chloride to a mixed carboxylic acid anhydride which is converted into the desired dicarbonate with excess tert-butyl carbonate. This process can be improved by replacing carboxylic anhydrides with sulfochlorides (CS-247845 and CS-247846). Other measures for the improvement of this process have also been proposed, for example the addition of a quaternary ammonium salt (CS-257157), the use of amines with an aliphatically bonded tertiary nitrogen, typically triethylamine, N,N-dimethylbenzylamine or N,N,N',N'-tetramethylethylenediamine (JP-90/103562), concentrating free sodium hydroxide solution below 10 mol % (JP-92/194326) or concentrating free sodium alcoholate below 3 mol % (JP-92/310648), the use of carbon dioxide under pressure (JP-92/279301) as well as the salt-free washing of the crude product prior to distilliation (JP-92/306261).

It has been found, however, that in spite of improvements all processes described above are still not entirely satisfactory. High yields, for example, are only achieved at elevated temperature, by prolonged reaction times or in the presence of considerable amounts of polar hydrophilic solvents such as tetrahydrofuran or dimethylformamide. Such polar hydrophilic solvents, however, which are used in pure or mixed form, cannot be readily recovered, if at all, and residues can enter into the waste water during washing. These processes therefore entail great ecological problems which can only be solved satisfactorily with considerable expenditure of costs. In addition, the quality of the crude products obtained leaves much to be desired, requiring a particularly careful and time-consuming fractional distillation to isolate the pure product. However, owing to the thermal sensitivity of DIBOC, distillation should, if possible, be avoided altogether or be at least carried out very rapidly, for example in a single step falling film evaporator.

CS-260076 proposes carrying out this process in the presence of pyridine and a quaternary ammonium salt. While this permits a reaction at room temperature, the yield is only 38.6% of theory and therefore an elevated temperature of preferably 50° C. is indicated in order to improve the yield. It has been found, however, that this induces the decomposition of the product and that said product contains considerable amounts of unreacted p-toluene sulfochloride, so that this method does not solve the problems described above.

EP 468 404 therefore proposes to replace tosyl chloride with mesyl chloride to improve the reactivity. This process should make it possible to produce good product qualities according to the description and the yield could even be increased by adding phase transfer catalysts, aromatic amines, or mixtures thereof.

In practice, however, it has been found that this latter process is also problematical. It has been found, for example, that very vigorous stirring of the reaction mixture is absolutely essential, which in laboratory practice is only possible with a special stirrer, and the yields decrease drastically in the scale-up. This problem is apparently caused at least partly by the physical properties of mesyl chloride which is a liquid of high specific density. In addition, mesyl chloride has a relatively high vapour pressure and is very caustic; it hydrolyses easily and reacts also with the alcoholate to be reacted under formation of methane sulfonic acid alkyl esters, which have a boiling point similar to that of the desired pyrocarbonic acid diesters so that their traces can hardly be removed at all by distillation. Because of this undesirable side reaction, mesyl chloride is also sometimes used in slight excess. And, finally, the resulting methane sulfonic acid cannot be isolated from the aqueous solution for recycling as easily as might be desired.

Surprisingly, it has now been found that pyrocarbonic acid diesters can in fact be obtained from ester carbonate and tosyl chloride in excellent yield and purity if this reaction is carried out in the presence of an ammonium salt and very small amounts of pyridine in a nonpolar inert solvent. Tosyl chloride and pyridine can also be replaced with structurally similar compounds, giving comparable results.

Accordingly, the invention relates to a process for the preparation of a pyrocarbonic acid diester of formula (I)

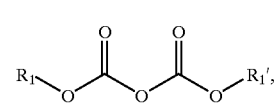

(I)

wherein $R_1$ and $R_1'$ are each independently of the other branched or straight-chain $C_1$–$C_{24}$ alkyl, $C_3$–$C_{24}$alkenyl, $C_3$–$C_{24}$alkynyl, $C_4$–$C_{12}$cycloalkyl, $C_4$–$C_{12}$cycloalkenyl or $C_7$–$C_{24}$aralkyl, each of which is unsubstituted or substituted by one or more than one substituent which is inert under the reaction conditions, by reacting at least one ester carbonate of formula (II)

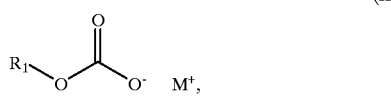
(II)

wherein $M^+$ is $Na^+$, $Li^+$, $K^+$ or $NR_2R_3R_4R_5^+$, and $R_2$ to $R_5$ are each independently of one another hydrogen, $C_1$–$C_{18}$alkyl, $C_5$–$C_{10}$cycloalkyl or $C_7$–$C_{18}$aralkyl, with 40–50 mol % of a sulfochloride of formula (IV)

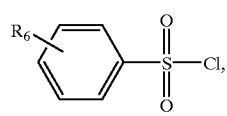
(IV)

wherein $R_6$ is —H, —$CH_3$, —$CH_2CH_3$, —Cl, —Br, —$OCH_3$ or —$NO_2$, in the presence of 0.8–5 mol % of a catalyst of formula (V)

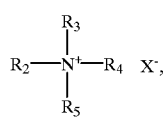
(V)

wherein
$R_2$ to $R_5$ have the meaning cited above, and
$X^-$ is a non-nucleophilic anion,
and with minor amounts of a heterocyclic aromatic amine in a nonpolar inert solvent,
in which process the amount of heterocyclic aromatic amine is 1–5 mol % and the reaction is carried out in the temperature range from –10° C. to +25° C.,
all molar amounts being based on 100 mol % of ester carbonate of formula (II).

$C_1$–$C_{18}$Alkyl is typically methyl, ethyl, n-propyl, isopropyl, n-butyl, sec-butyl, isobutyl, tert-butyl, n-pentyl, 2-pentyl, 3-pentyl, 2,2-dimethylpropyl, n-hexyl, n-octyl, 1,1,3,3-tetra-methylbutyl, 2-ethylhexyl, nonyl, decyl, dodecyl, tetradecyl, hexadecyl or octadecyl. $C_1$–$C_{24}$Alkyl can additionally be, for example, eicosyl, heneicosyl, docosyl or tetracosyl.

$C_3$–$C_{24}$Alkenyl is $C_3$–$C_{24}$alkyl which is mono- or polyunsaturated and wherein two or more than two double bonds can be isolated or conjugated, for example allyl, 2-propen-2-yl, 2-buten-1-yl, 3-buten-1-yl, 1,3-butadien-2-yl, 2-penten-1-yl, 3-penten-2-yl, 2-methyl-1-buten-3-yl, 2-methyl-3-buten-2-yl, 3-methyl-2-buten-1-yl, 1,4-pentadien-3-yl, or the different isomers of hexenyl, octenyl, nonenyl, decenyl, dodecenyl, tetradecenyl, hexadecenyl, octadecenyl, eicosenyl, heneicosenyl, docosenyl, tetracosenyl, hexadienyl, octadienyl, nonadienyl, decadienyl, dodecadienyl, tetradecadienyl, hexadecadienyl, octadecadienyl, eicosadienyl, heneicosadienyl, docosadienyl or tetracosadienyl.

$C_4$–$C_{12}$Cycloalkyl is, for example, a monocyclic cycloalkyl, typically cyclobutyl, cyclopentyl, cyclohexyl, trimethylcyclohexyl or menthyl, or a polycyclic cycloalkyl, typically thujyl, bornyl, 1-adamantyl or 2-adamantyl.

$C_4$–$C_{12}$Cycloalkenyl is $C_4$–$C_{12}$cycloalkyl which is mono- or polyunsaturated and wherein two or more than two double bonds can be isolated or conjugated, typically 2-cyclobuten-1-yl, 2-cyclopenten-1-yl, 2-cyclohexen-1-yl, 3-cyclohexen-1-yl, 2,4-cyclohexadien-1-yl, 1-p-menthen-8-yl, 4(10)-thujen-10-yl, 2-norbornen-1-yl, 2,5-norbornadien-1-yl or 7,7-dimethyl-2,4-norcaradien-3-yl.

$C_3$–$C_{24}$Alkynyl is $C_3$–$C_{24}$alkyl or $C_3$–$C_{24}$alkenyl, each of which is once or more than once doubly unsaturated and wherein the triple bonds can be isolated or conjugated among themselves or with double bonds, typically 1-propin-3-yl, 1-butin-4-yl, 1-pentin-5-yl, 2-methyl-3-butin-2-yl, 1,4-pentadiin-3-yl, 1,3-pentadiin-5-yl, 1-hexin-6-yl, cis-3-methyl-2-penten-4-in-1-yl, trans-3-methyl-2-penten-4-in-1-yl, 1,3-hexadiin-5-yl, 1-octin-8-yl, 1-nonin-9-yl, 1-decin-10-yl or 1-tetracosin-24-yl.

$C_7$–$C_{18}$Aralkyl is typically 2-benzyl-2-propyl, β-phenylethyl, α,α-dimethylbenzyl, ω-phenyl-butyl, ω-phenyloctyl, ω-pentyldodecyl or 3-methyl-5-(1',1',3',3'-tetramethyl)butylbenzyl. $C_7$–$C_{24}$Aralkyl can additionally be, for example, 2,4,6-tri-tert-butylbenzyl or 1-(3,5-dibenzyl-phenyl)-3-methyl-2-propyl.

If $R_1$ and $R_1'$ are substituted, then the substituents can be such that they are inert under the reaction conditions. Typical examples of inert substituents are halogen atoms, for example fluoro or chloro, ether groups, such as —O—$R_2$ or —(O—$C_1$–$C_6$)$_n$—O—$C_1$–$C_{18}$alkyl, typically methoxy, ethoxy, butoxy, octadecyloxy, 3-oxahept-1-yloxy, or monomethoxy polyethylene radicals, monoethoxy polyethylene glycol radicals, monomethoxy polypropylene glycol radicals or monoethoxy polypropylene radicals, amino groups, such as —$NR_2R_3$, typically dimethylamino, methylethylamino, diethylamino, dibutylamino, butyldodecylamino, dioctadecylamino or methyl(3-azahept-1-yl)amino, thioether groups, such as —S—$R_2$ ($R_2 \neq H$), typically methylthio, ethylthio, butylthio or octadecylylthio, cyano, nitro or α,β-unsaturated ketone radicals. Known pyrocarbonic acid diesters of formula (I), wherein $R_1$ and $R_1'$ carry inert substituents, are e.g. di(1,1,1,3,3,3-hexafluoro-2-propyl)dicarbonate or di[1-methyl-3-(2,6,6-trimethyl-3-oxo-1-cyclohexen-1-yl)-2-propenyl]dicarbonate.

Heterocyclic aromatic amines are, for example, pyridine, α-, β- or γ-picoline, 2,4-, 2,6-, 3,4- or 3,5-lutidine, collidine or quinoline.

Nonpolar inert solvents are those having a dielectric constant $\varepsilon \leq 10$ and which are immiscible with water and which, under the conditions of this process, react neither with the ester carbonate of formula (II) nor with the sulfochloride of formula (IV), for example aromatic hydrocarbons, typically benzene, toluene, xylene, mesitylene or ethylbenzene, aliphatic hydrocarbons, typically pentane, hexane, cyclohexane, heptane, octane, decane or decahydronaphthalene, noncyclic ethers, typically diethyl ether, diisopropyl ether, diisopropyl ether or diisobutyl ether, or mixtures thereof, for example special boiling-point spirit or ®Shell-Sol products.

Sulfochlorides of formula (IV) are preferably benzene sulfochloride and p-toluene sulfochloride.

Preferred catalyst cations are those wherein $R_2$ to $R_5$ are each independently of one another methyl, ethyl, butyl, benzyl, octyl, dodecyl or octadecyl, in particular those wherein the sum of the carbon atoms in the groups $R_{41}$ to $R_{44}$ is from 10 to 24.

Particularly preferred catalyst cations are those wherein $R_2$ to $R_5$ are butyl, or $R_2$ and $R_3$ are methyl, $R_4$ is methyl or ethyl, and $R_5$ is benzyl, dodecyl or octadecyl.

Non-nucleophilic catalyst anions $Y^-$ are typically $Cl^-$, $Br^-$, $F^-$, $J^-$, $NO_3^-$, $ClO_4^-$, $HSO_4^-$, $PF_6^-$, $B(C_6H_5)_4^-$ or $BF_4^-$.

Catalyst anions are preferably bromide and chloride, in particular chloride.

A particularly preferred catalyst of formula (V) is benzyltrimethylammonium chloride.

Heterocyclic aromatic amine is preferably pyridine.

Solvents are preferably aromatic hydrocarbons.

Particularly preferred solvents are toluene and xylene.

The preferred amount of sulfochloride of formula (IV) is c. 45 mol %, based on (II).

The preferred amount of catalyst of formula (V) is 1.0–1.5 mol %, based on (II).

The preferred amount of heterocyclic aromatic amine is 1–3 mol %, based on (II). The particularly preferred amount of heterocyclic aromatic amine is c. 3 mol %, based on (II). The amount of solvent is not critical. It is preferred to use exactly the amount of solvent required to make the reaction mixture readily stirrable during the entire reaction, which amount can differ depending on the pyrocarbonic acid diester to be prepared. The reaction temperature is preferably from 0° C. to +20° C.

The reaction temperature is particularly preferably from 0° C. to +10° C.

The reaction time depends on the amounts of catalyst and heterocyclic aromatic amine as well as on the temperature. The reaction is usually completed after ½ to 100 hours, preferably after ½ to 10 hours.

All the chemicals required are known and are commercially available or can be prepared according to known methods.

The process can be carried out most simply by introducing the solvent and all educts (II) to (V) concurrently or in succession and in any order into the reaction vessel at the reaction temperature. Conveniently, at least part of the solvent is placed in the reaction vessel first and the sulfochloride is added last.

The ester carbonate of formula (II) is preferably prepared in situ according to known processes, for example as indicated in the above literature references. In this process, an alcoholate of formula (VI)

(VI)

is added to a solvent, which may also be done by reacting an alcohol $R_1OH$ with an alkali metal M or an alkali metal hydride MH in the above solvent in an inert atmosphere. Carbon dioxide is then introduced, where appropriate under pressure, until the ester carbonate of formula (II) is formed. It may be expedient to deviate from the temperature range for the preparation of the pyrocarbonic acid diester. In particular, elevated temperatures, e.g. reflux temperature, are suitable to accelerate and complete the alcoholate formation from alcohol and metal, and lower temperatures, e.g. –15° C., are suitable to moderate the alcoholate formation from alcohol and metal hydride.

To the solution or suspension of the ester carbonate of formula (II) are then added, with stirring, the catalyst of formula (V), the heterocyclic aromatic amine and the sulfochloride of formula (IV) in the amounts indicated above at the specified reaction temperature from –10° C. to +25° C. If required, the reaction can be observed using gas chromatography.

The reaction mixture can subsequently also be processed in standard manner, typically by washing with dilute aqueous acid and/or with water and by concentrating the separated organic phase by evaporation. Prior to being concentrated by evaporation, the organic phase can be treated with customary known agents, typically drying agents such as anhydrous sodium sulfate or magnesium sulfate, or adsorbents, such as activated carbon or bleaching earths.

The pyrocarbonic acid diesters of formula (I) are obtained in high yield and purity. If desired, they can additionally be distilled, and because of the high purity of the crude product the distillation can be carried out particularly gently and rapidly.

Owing to the improved reactivity achieved by this invention it is possible to use amounts of sulfochloride up to near the stoichiometrically determined limit of 50 mol % without any contamination of the product with unreacted sulfochloride and without any substantial prolongation of the reaction time. A preferred amount of sulfochloride is c. 45 mol %, based on 100 mol % of ester carbonate of formula (II).

Using mixtures of ester carbonates. of formula (II), asymmetrical pyrocarbonic acid diesters of formula (I) can be obtained, wherein $R_1$ and $R_1'$ are different. In this case it is expedient to use a molar ratio of 1:1, one ester carbonate preferably being added first and the other ester carbonate being added only after the sulfochloride. Depending on the end use requirement, such pyrocarbonic acid diesters can be used as mixtures of homologues, or the asymmetrical compound can be isolated, for example by fractional distillation.

Known pyrocarbonic acid diesters are those of formulae (VI)

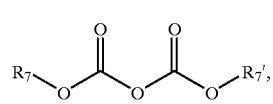

(VI)

wherein $R_7$ as well as $R_7'$ are $C_1$–$C_{24}$alkyl which is not branched in a-position and which is unsubstituted or substituted by one or more than one substituent which is inert under the reaction conditions, and (VII)

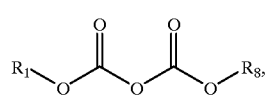

(VII)

wherein
$R_1$ is as defined above, and $R_8$ is branched or straight-chain $C_3$–$C_{24}$alkenyl, $C_3$–$C_{24}$alkynyl, $C_4$–$C_{12}$cycloalkyl, $C_4$–$C_{12}$cycloalkenyl or $C_7$–$C_{24}$aralkyl, each of which is unsubstituted or substituted by one or more than one substituent which is inert under the reaction conditions,
or $C_7$–$C_{24}$alkyl which is branched in α-position,
$R_1$ and $R_8$ in formula (VII) being combined as indicated in Table 1:

TABLE 1

Known compounds of formula (VII)

| Compound | CA Reg. No. | R₁ | R₈ |
| --- | --- | --- | --- |
| VI a | 4525-34-2 | 2-propinyl | 2-propinyl |
| VI b | 5944-45-6 | methyl | allyl |
| VI c | 5944-46-7 | allyl | benzyl |
| VI d | 5944-47-8 | ethyl | benzyl |
| VI e | 24424-99-5 | tert-butyl | tert-butyl |
| VI f | 24425-00-1 | isopropyl | isopropyl |
| VI g | 31139-36-3 | benzyl | benzyl |
| VI h | 32813-64-2 | 2-benzyl-2-propyl | 2-benzyl-2-propyl |
| VI i | 55130-19-3 | isopropyl | tert-butyl |
| VI j | 61114-48-5 | cyclohexyl | cyclohexyl |
| VI k | 61114-49-6 | 2-butyl | 2-butyl |
| VI l | 65815-74-9 | 1-adamantyl | 1-adamantyl |
| VI m | 68835-89-2 | 2-methyl-2-butyl | 2-methyl-2-butyl |
| VI n | 115491-93-5 | allyl | allyl |
| VI o | 116055-32-4 | ethyl | 3,4-dichlorobenzyl |
| VI p | 116977-36-7 | ethyl | allyl |
| VI q | 125372-96-5 | 1,1,1,3,3,3-hexafluoro-2-propyl | 1,1,1,3,3,3-hexafluoro-2-propyl |
| VI r | 133389-94-3 | 3-butenyl | 3-butenyl |
| VI s | 146919-25-7 | tert-butyl | 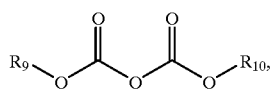 |
| VI t | 149364-65-8 | cyclopentyl | cyclopentyl |
| VI u | 160788-62-5 | allyl | 1-methylethenyl |

The other pyrocarbonic acid diesters of formula (I) which can be prepared according to the process of this invention are still novel.

Accordingly, the invention also relates to pyrocarbonic acid diesters of formula (VIII)

wherein $R_9$ is branched or straight-chain $C_1$–$C_{24}$alkyl, $C_3$–$C_{24}$alkenyl, $C_3$–$C_{24}$alkynyl, $C_4$–$C_{12}$cycloalkyl, $C_4$–$C_{12}$cycloalkenyl or $C_7$–$C_{24}$aralkyl, each of which is unsubstituted or substituted by one or more than one substituent which is inert under the reaction conditions, and $R_{10}$ is independently of $R_9$ branched or straight-chain $C_3$–$C_{24}$alkenyl, $C_3$–$C_{24}$alkynyl, $C_4$–$C_{12}$cycloalkyl, $C_4$–$C_{12}$cycloalkenyl or $C_7$–$C_{24}$aralkyl, each of which is unsubstituted or substituted by one or more than one substituent which is inert under the reaction conditions, or $C_3$–$C_{24}$alkyl which is branched in α-position, with the proviso that it is not possible that $R_9$ is $R_1$ and $R_{10}$ is $R_8$ at the same time, wherein $R_1$ and $R_8$ have the meaning indicated in Table 1.

Preferred pyrocarbonic acid diesters are those of formula (I), wherein $R_1$ and $R_1'$ are attached at the oxygen atom of the dicarbonate group with a secondary or tertiary carbon atom, as well as those wherein $R_1$ and $R_1'$ are unsaturated in β-position, in particular di-tert-butyl dicarbonate, di-tert-pentyl dicarbonate, di-5-nonyl dicarbonate, diallyl dicarbonate, di(2-methyl-3-butin-2-yl) dicarbonate or di(2-methyl-3-buten-2-yl) dicarbonate.

Particularly preferred pyrocarbonic acid diesters of formula (I) are di-tert-pentyl dicarbonate, di-5-nonyl dicarbonate, diallyl dicarbonate, di(2-methyl-3-buten-2-yl) dicarbonate or di(2-methyl-3-butin-2-yl) dicarbonate.

The pyrocarbonic acid diesters of formula (VIII) can be used for any known purpose and can be preferably used for the preparation of soluble pigment precursors, such as those disclosed in EP 648 770 and EP 648 817.

Preferred pigment precursors for the preparation of which pyrocarbonic acid diesters of formula (VIII) can be used, are those of formula (IX)

$$A(B)_x \quad \text{(IX)},$$

wherein x is an integer from 1 to 4,

A is the radical of a chromophore of the quinacridone, anthraquinone, indanthrone, perylene, indigo, quinophthalone, isoindolinone, isoindoline, dioxazine, azo, phthalocyanine or diketopyrrolopyrrole series, which radical A contains x N-atoms which are conjugated with, or adjacent to, at least one carbonyl group, and B is a group of formula (X)

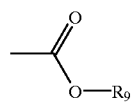

which is linked to one of these N-atoms and wherein $R_9$ has the meaning cited above.

The chromophore radicals and substitution patterns of such pigment precursors, as well as pigment precursors themselves, are known from, inter alia, EP 654 711.

The following Examples illustrate the invention in more detail:

EXAMPLES 1–10

(General Instruction)

0.1 mol of alkali metal alkoxide is suspended (or dissolved) in 150 ml of toluene, and 1.2 mol of $CO_2$ are then introduced at 0–10° C. 228 mg of benzyltrimethylammonium chloride and 240 mg of pyridine are added to the stirred suspension (solution) and after 15 min the toluene-4-sulfochloride is added in the amount indicated below. The resulting suspension is stirred overnight. 25 ml of 5% aqueous $H_2SO_4$ are then added and the thick suspension so obtained is stirred for 30 min. Subsequently, the organic phase is separated, washed with 3×150 ml of water, dried over $MgSO_4$ and treated with activated carbon. The colourless solution is then concentrated under vacuum, giving the pyrocarbonic acid diesters in good purity with the yields and chromatographic retention values indicated in Table 2.

TABLE 2

Examples 1–10

| Example No. | $R_1 = R_1{'}$ | mol (IV) | Yield [based on (IV)] | $R_f$ (silica gel, hexane:$CH_2Cl_2$ 1:1) |
|---|---|---|---|---|
| 1 | tert-butyl | 0.40 | 85% | 0.55 |
| 2 | 2-methyl-2-butyl | 0.43 | 81% | 0.61 |
| 3 | 3-ethyl-3-pentyl | 0.42 | 58% | 0.63 |
| 4 | 2-methyl-2-hexyl | 0.42 | 37% | 0.67 |
| 5 | 2-benzyl-2-propyl | 0.40 | 29% | 0.50 |
| 6 | isopropyl | 0.40 | 55% | 0.62 |
| 7 | 9-methyl-9-octadecyl | 0.43 | 93% | 0.45 |
| 8 | 2-methyl-2-decyl | 0.42 | 65% | 0.32 |
| 9 | 2-methyl-2-nonadecyl | 0.43 | 98% | 0.19 |
| 10 | 5-nonyl | 0.40 | 75% | 0.76 |

The $^1$H-nuclear magnetic resonance spectra ($^1$H-NMR) of the products are in accordance with the known spectra or are in keeping with the expectations.

EXAMPLE 11

Example 1 is repeated, but replacing 0.40 mol of toluene-4-sulfochloride with 0.45 mol of toluene-4-sulfochloride, giving di-tert-butyl dicarbonate in comparable quality.

EXAMPLE 12

Example 1 is repeated, but replacing 0.40 mol of toluene-4-sulfochloride with 0.48 mol of toluene-4-sulfochloride, giving di-tert-butyl dicarbonate in comparable quality.

EXAMPLE 13

A solution of 84.1 g (1 mol) of 2-methyl-3-butin-2-ol in 1.75 l of toluene is cooled to 3° C. and 40 g (1 mol) of 60% sodium hydride are then added in increments in an inert gas atmosphere such that the temperature does not rise above 10° C. After the addition of 250 ml of toluene, the mixture is stirred overnight at 18° C. The brown solution is cooled to 5° C. and 101.7 g (2.3 mol) of $CO_2$ are then introduced at 5–10° C. The reaction mixture is warmed to 18° C. and then 3.2 g (0.014 mol) of benzyltrimethylammonium chloride, 2.4 g (0.03 mol) of pyridine and 82.8 g (0.43 mol) of toluene-4-sulfochloride are added in succession. The resulting suspension is stirred for three days at room temperature. 260 ml of 5% aqueous $H_2SO_4$ are then added dropwise at 5° C. such that the temperature does not rise above 10° C. The organic phase is separated, washed with 5×400 ml of water, dried over $Na_2SO_4$ and concentrated under vacuum. The crude product (94.8 g) is treated with hexane, affording 70 g (59% of theory, calculated on the basis of the toluene-4-sulfochloride) of a pure white di(2-methyl-3-butin-2-yl) dicarbonate having a m.p. of 102.8° C. The elemental analysis and the $^1$H-NMR spectrum are in keeping with the expectations.

EXAMPLE 14

Example 13 is repeated, but starting from 2-methyl-3-buten-2-ol instead of from 2-methyl-3-butin-2-ol and using 0.50 mol of toluene-4-sulfochloride instead of 0.40 mol of toluene-4-sulfochloride.

Good quality di(2-methyl-3-buten-2-yl) dicarbonate is obtained in a 61% yield of theory (calculated on the basis of the toluene-4-sulfochloride).

The $^1$H-NMR spectrum is in keeping with the expectations.

EXAMPLE 15

Example 13 is repeated, but starting from 3-methyl-2-buten-1-ol instead of from 2-methyl-3-butin-2-ol, giving di(3-methyl-2-buten-1-yl) dicarbonate having an $^1$H-NMR spectrum which is in keeping with the expectations.

EXAMPLE 16

6.6 g (0.15 mol) of $CO_2$ are introduced into a suspension of 11.22 g (0.1 mol) of potassium tert-butylate in 150 ml of toluene at 0–10° C. 228 mg of benzyltrimethyl-ammonium chloride, 240 mg of pyridine and, after 15 min, 7.6 g (0.04) mol of toluene-4-sulfochloride are added to the stirred suspension. The resulting suspension is stirred overnight. 25 ml of 5% aqueous $H_2SO_4$ are added and the thick suspension so obtained is then stirred for 30 min. The organic phase is then separated, washed with 3×150 ml of water, dried over $MgSO_4$ and treated with activated carbon. Subsequently, the colourless solution is concentrated under vacuum and the colourless residue is distilled at 55° C./$10^{-2}$ mbar. The distilled fraction affords 6.37 g of pure di-tert-butyl dicarbonate; yield 73% of theory (calculated on the basis of the toluene-4-sulfochloride).

EXAMPLE 17

6.6 g (0.15 mol) of $CO_2$ are introduced into a suspension of 11.22 g (0.1 mol) of potassium tert-butylate in 150 ml of toluene at 0–10° C. 228 mg of benzyltrimethyl-ammoniume chloride, 240 mg of pyridine and, after 15 min, 8.58 g (0.045) mol of toluene-4-sulfochloride are added to the stirred suspension. The resulting suspension is stirred overnight. 25 ml of 5% aqueous $H_2SO_4$ are added and the thick suspension so obtained is stirred for 30 min. The organic phase is then separated, washed with 3×150 ml of water, dried over MgSO₄ and treated with activated carbon. Subsequently, the colourless solution is concentrated under vacuum and the colourless residue is destilled at 55° C./10⁻² mbar. The distilled fraction affords 6.37 g of pure di-tert-butyl dicarbonate; yield 80% of theory (calculated on the basis of the toluene-4-sulfochloride).

EXAMPLE 18

228 mg of benzyltrimethylammonium chloride, 240 mg of pyridine and, after 15 min, 7.6 g (0.04 mol) of toluene-4-sulfochloride are added to a stirred suspension of 14.01 g (0.1 mol) of sodium tert-butyl carbonate in 150 ml of toluene at 20° C. The resulting suspension is stirred for a further 24 h at 40° C. 25 ml of 5% aqueous H₂SO₄ are added and the thick suspension so obtained is stirred for 30 min. The organic phase is then separated, washed with 3×150 ml of water, dried over MgSO₄ and treated with activated carbon. Subsequently, the colourless solution is concentrated under vacuum and the colourless residue is distilled at 55° C./10⁻² mbar.

The distilled fraction affords 7.2 g of pure di-tert-butyl dicarbonate; yield 82.5 % of theory (calculated on the basis of the toluene-4-sulfochloride).

Comparative Example 1
(Relating to Example 18/reaction Conditions According to CS 260076, Example 2)

228 mg of benzyltrimethylammonium chloride, 10 ml of pyridine and, after 15 min, 7.6 g (0.04 mol) of toluene-4-sulfochloride are added to a stirred suspension of 14.01 g (0.1 mol) of sodium tert-butyl carbonate in 150 ml of toluene at 20° C. The resulting suspension is stirred for a further 1.5 h at 50° C. 25 ml of 5% aqueous H₂SO₄ are added and the thick suspension so obtained is stirred for 30 min. The organic phase is then separated, washed with 3×150 ml of water, dried over MgSO₄ and treated with activated carbon. Subsequently, the brown solution is concentrated under vacuum and the dark brown residue is distilled at 55° C./10⁻² mbar. The distilled fraction affords 5.8 g of a mixture consisting of 93.7% of di-tert-butyl dicarbonate and 6.3% of unreacted toluene-4-sulfochloride. The di-tert-butyl dicarbonate yield in the mixture is 62.7% of theory (calculated on basis of the toluene-4-sulfochloride).

What is claimed is:

1. A soluble pigment derivative of formula (IX)

A(B)$_x$         (IX), wherein
x is an integer from 1 to 4,
A is the radical of a quinacridone, indigo, dioxazine or azo pigment, in which radical A there are from 1 to 4 N-atoms which are conjugated with, or adjacent to, at least one carbonyl group, and
B is a group of formula (X)

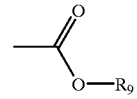
        (X)

which is linked to at least one of the N-atoms and wherein R₉ is a branched C₅–C₂₀alkyl group in which the carbon atom attached to the oxygen atom is a secondary carbon atom.

2. A soluble pigment derivative according to claim 1, wherein R₉ is 2-pentyl, 3-pentyl, 2-ethylhexyl or secondary nonyl, decyl, dodecyl, tetradecyl, hexadecyl, octadecyl eicosyl, heneicosyl, docosyl or tetracosyl.

3. A soluble pigment derivative according to claim 2, wherein R₉ is 5-nonyl.

4. A soluble pigment derivative according to claim 2, wherein R₉ is 3-pentyl.

5. A soluble pigment derivative according to claim 2, wherein R₉ is 2-ethylhexyl.

* * * * *